United States Patent
Jahns et al.

(10) Patent No.: US 10,028,809 B2
(45) Date of Patent: Jul. 24, 2018

(54) MULTI SECTIONAL DENTAL ZIRCONIA MILLING BLOCK, PROCESS OF PRODUCTION AND USE THEREOF

(71) Applicant: 3M INNOVATIVE PROPERTIES COMPANY, Saint Paul, MN (US)

(72) Inventors: Michael Jahns, Gilching (DE); Holger Hauptmann, Sindelsdorf (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 296 days.

(21) Appl. No.: 14/436,109

(22) PCT Filed: Oct. 2, 2013

(86) PCT No.: PCT/US2013/062960
§ 371 (c)(1),
(2) Date: Apr. 16, 2015

(87) PCT Pub. No.: WO2014/062375
PCT Pub. Date: Apr. 24, 2014

(65) Prior Publication Data
US 2015/0282905 A1    Oct. 8, 2015

(30) Foreign Application Priority Data
Oct. 17, 2012  (EP) .................................... 12188852

(51) Int. Cl.
*A61C 13/00*  (2006.01)
*A61K 6/02*   (2006.01)
(Continued)

(52) U.S. Cl.
CPC ........ *A61C 13/0006* (2013.01); *A61C 13/082* (2013.01); *A61K 6/024* (2013.01);
(Continued)

(58) Field of Classification Search
CPC .. A61C 13/0006; A61C 13/082; A61K 6/024; A61K 6/0245; A61K 6/025; B32B 19/00;
(Continued)

(56) References Cited

U.S. PATENT DOCUMENTS 5,169,513 A    12/1992  Mase
5,453,262 A     9/1995  Dawson
(Continued)

FOREIGN PATENT DOCUMENTS

DE       20316004       3/2004
WO    WO 2001-13862     3/2001
(Continued)

OTHER PUBLICATIONS

International Search report for PCT International Application No. PCT/US2013/062960 dated Jan. 22, 2014, 3 pages.

*Primary Examiner* — Nicholas Lucchesi

(57) ABSTRACT

The invention relates to a porous dental milling block comprising at least two geometrically defined Material Sections A and B, Material Section A comprising a tetragonal zirconia crystal phase in an amount A-T in % and a cubic zirconia crystal phase in an amount A-C in %, Material Section B comprising tetragonal zirconia crystal phase in an amount B-T in % and cubic zirconia crystal phase in an amount B-C in %, wherein (amount of tetragonal phase A-T in %)/(amount of cubic phase content A-C in %)>1 and (amount of tetragonal phase content B-T in %)/(amount of cubic phase content B-C in %)<1.
The invention also relates to a process of production of the porous dental milling block and its use for producing a dental article.

12 Claims, 2 Drawing Sheets

(51) Int. Cl.
*B32B 18/00* (2006.01)
*C04B 35/486* (2006.01)
*C04B 35/624* (2006.01)
*C04B 35/626* (2006.01)
*C04B 35/632* (2006.01)
*C04B 35/634* (2006.01)
*C04B 38/00* (2006.01)
*C01G 25/02* (2006.01)
*B82Y 30/00* (2011.01)
*A61C 13/08* (2006.01)
*C04B 111/00* (2006.01)

(52) U.S. Cl.
CPC ............ *A61K 6/025* (2013.01); *A61K 6/0245* (2013.01); *B32B 18/00* (2013.01); *B82Y 30/00* (2013.01); *C01G 25/02* (2013.01); *C04B 35/486* (2013.01); *C04B 35/624* (2013.01); *C04B 35/6263* (2013.01); *C04B 35/6269* (2013.01); *C04B 35/632* (2013.01); *C04B 35/63424* (2013.01); *C04B 35/63488* (2013.01); *C04B 38/0054* (2013.01); *C01P 2002/52* (2013.01); *C01P 2004/54* (2013.01); *C04B 2111/00836* (2013.01); *C04B 2235/3206* (2013.01); *C04B 2235/3208* (2013.01); *C04B 2235/3217* (2013.01); *C04B 2235/3224* (2013.01); *C04B 2235/3225* (2013.01); *C04B 2235/3227* (2013.01); *C04B 2235/3229* (2013.01); *C04B 2235/3232* (2013.01); *C04B 2235/3239* (2013.01); *C04B 2235/3241* (2013.01); *C04B 2235/3256* (2013.01); *C04B 2235/3262* (2013.01); *C04B 2235/3272* (2013.01); *C04B 2235/3275* (2013.01); *C04B 2235/3418* (2013.01); *C04B 2235/449* (2013.01); *C04B 2235/5409* (2013.01); *C04B 2235/5454* (2013.01); *C04B 2235/6023* (2013.01); *C04B 2235/61* (2013.01); *C04B 2235/612* (2013.01); *C04B 2235/72* (2013.01); *C04B 2235/762* (2013.01); *C04B 2235/765* (2013.01); *C04B 2235/77* (2013.01); *C04B 2235/945* (2013.01); *C04B 2235/95* (2013.01); *C04B 2235/96* (2013.01); *C04B 2235/9646* (2013.01); *C04B 2235/9653* (2013.01); *C04B 2237/348* (2013.01); *C04B 2237/582* (2013.01); *C04B 2237/84* (2013.01); *Y10T 428/24997* (2015.04)

(58) Field of Classification Search
CPC ..... C01G 25/02; C04B 35/486; C04B 35/624; C04B 35/6263; C04B 35/632; C04B 35/6269; C04B 35/63424; C04B 35/63488; C04B 38/0054
See application file for complete search history.

(56) References Cited

U.S. PATENT DOCUMENTS

| | | | |
|---|---|---|---|
| 5,652,192 A | 7/1997 | Matson | |
| 6,709,694 B1 | 3/2004 | Suttor | |
| 7,985,119 B2 | 7/2011 | Basler | |
| 8,141,217 B2 | 3/2012 | Gubler | |
| 8,178,012 B1* | 5/2012 | Khan | A61C 13/082 264/16 |
| 2006/0117989 A1 | 6/2006 | Hauptmann | |
| 2008/0303181 A1* | 12/2008 | Holand | A61C 13/0022 264/16 |
| 2010/0041542 A1* | 2/2010 | Rolf | A61C 8/0012 501/104 |
| 2010/0130346 A1* | 5/2010 | Laine | B82Y 30/00 501/105 |
| 2011/0269618 A1 | 11/2011 | Knapp | |
| 2012/0156472 A1 | 6/2012 | Brannvall | |
| 2015/0238291 A1* | 8/2015 | Hauptmann | A61C 13/0022 428/64.1 |
| 2017/0020639 A1* | 1/2017 | Jahns | A61C 8/0012 |

FOREIGN PATENT DOCUMENTS

| | | |
|---|---|---|
| WO | WO 2002-45614 | 6/2002 |
| WO | WO 2009-014903 | 1/2009 |
| WO | WO 2013-022612 | 2/2013 |
| WO | WO 2013-053181 | 4/2013 |
| WO | WO 2013-055432 | 4/2013 |
| WO | WO 2014-021940 | 2/2014 |

* cited by examiner

MULTI SECTIONAL DENTAL ZIRCONIA MILLING BLOCK, PROCESS OF PRODUCTION AND USE THEREOF

CROSS REFERENCE TO RELATED APPLICATIONS

This application is a national stage filing under 35 U.S.C. 371 of PCT/US2013/062960, filed 2 Oct. 2013, which claims priority to European Application No. 12188852.3, filed 17 Oct. 2012, the disclosures of which are incorporated by reference in their entirety herein.

SUMMARY OF INVENTION

The invention is directed to a multi sectional dental zirconia milling block, processes for its production and use for producing dental articles, the dental zirconia milling block comprising at least two defined sections having different translucencies.

BACKGROUND

Natural teeth show a quite complex gradient in translucency, beginning from translucent (enamel) to nearly opaque (dentin) from the outer to the inner area. Translucency is therefore a desired property of dental materials where esthetic matters.

Currently, in trying to achieve highly esthetic ceramic restoration, the high strength ceramic (e.g. zirconia) material is typically veneered with a low strength high translucent and typically glass-ceramic based veneering material.

In most cases, the veneering step is done by a skilled lab technician and is often time consuming and expensive. Due to the weakness of the veneering porcelain chipping is often observed in a variety of clinical cases.

Another way to produce dental restorations is using a so-called monolithic zirconia material without applying a veneering step. This possibility is typically chosen for situations where esthetics plays only a minor role (e.g. in the posterior regions of the dental situation).

Zirconia based dental restorations are typically produced via a CAD/CAM process:
  A dental restoration is milled out of a pre-sintered zirconia mill blank.
  Afterwards the esthetic of the dental restoration is increased by coloring the material with a suitable coloring liquid.
  The dental restoration is finished by sintering and polishing.

In the field of glass ceramics a couple of layered blocks with different degrees of translucency are meanwhile commercial available.

E.g. Vita Company offers a so-called TriLux™-block (having planar layers) as well as the so-called TrueLife™ block (having a conical core).

These blocks are designed for so-called chair-side dental restorations, that is, dental restorations which are manufactured when the patient to be treated is still in the office of the dentist.

Producing these kinds of blocks out of zirconia materials having different translucencies is, however, not possible due to different sintering temperatures needed for sintering the individual materials.

The sintering of tetragonal zirconia (e.g. 3Y-TZP: Tosoh Corp., Japan) is typically done in a range of 1350° C. to 1550° C., whereas the sintering of cubic zirconia or fully stabilized zirconia (e.g. 10Y-ZP: supplier e.g. Tosoh Corp., Japan) is typically done at a temperature above 1550° C.

During a co-firing process, a zirconia block being prepared out of these materials will typically break or show fractures.

In U.S. application 61/545,243 (3M IPC) aerogels, calcined and crystalline articles and methods of making the same are described.

US 2011/0269618 (Knapp et al.) relates to nano-crystalline dental ceramics, where the nanocrystals are formed by vaporization.

US 2012/0156472 (Brännvall et al.) relates to a dental application body comprising an oxide ceramic containing a bulk material containing an oxide ceramic and at least one coating containing yttrium oxide and/or cerium oxide stabilized zirconium oxide. It is stated that the yttrium oxide and/or cerium oxide stabilized zirconium oxide coating powder forming the basic raw material for the coating has a particle size of between 0.20 and 1.00 µm. The thickness of the coating is typically with a range of 5 to 300 µm. The dental application body is said to have improved aging capability and can be used as bone anchored implant.

DESCRIPTION OF INVENTION

There is a general need for means which facilitate the production of highly aesthetic dental articles, especially dental replacement parts like crowns, bridges, implants, inlays, veneers, etc.

In particular, it would be desirable to have a dental milling block available which facilitates the production of dental replacement parts without the need for a further veneering step, a step which is typically needed to mimic the appearance of a natural tooth.

Thus, it would be desirable to have a machinable multi-sectional block where the individual sections are made of a sufficiently hard material having different translucencies. Further, it should be possible to sinter the article machined out of that block without cracks.

Further, it would be desirable to be able to produce this block without the need for the application of a so-called hot isostatic pressing step (HIP).

This object can be achieved by bringing into contact a composition comprising high strength tetragonal zirconia crystallites (t-ZrO2) with a composition comprising highly translucent cubic zirconia crystallites (c-ZrO2) and pre-sinter the achieved body, optionally followed by a co-firing step to final density.

Each of the compositions may have different blends of t-ZrO2 and c-ZrO2 depending on the desired properties.

Thus, in one aspect the invention relates to a porous dental milling block comprising at least two geometrically defined Material Sections A and B,
  Material Section A comprising a tetragonal zirconia crystal phase in an amount A-T in % and a cubic zirconia crystal phase in an amount A-C in %,
  Material Section B comprising tetragonal zirconia crystal phase in an amount B-T in % and cubic zirconia crystal phase in an amount B-C in %,
  wherein (amount of tetragonal phase $A\text{-}T$ in %)/(amount of cubic phase content $A\text{-}C$ in %)>1 and (amount of tetragonal phase $B\text{-}T$ in %)/(amount of cubic phase $B\text{-}C$ in %)<1, In another aspect the invention relates to a porous dental milling block as described in the present text, the material of Material Section A and B being characterized by the following properties:
- showing a N2 adsorption and/or desorption behaviour of isotherm IV according to IUPAC classification,
- the sintering temperature being in a range of 1200 to 1400° C.

Yet a further aspect of the invention is related to a process of producing a porous dental milling block having at least two material sections differing by their content of cubic phase and tetragonal phase as described in the present text, the process comprising the steps of
- casting a sol (I) containing zirconia crystallites into a mould (I), the zirconia crystallites having a crystal phase (1),
- transferring the sol (I) to a gel body (I),
- optionally transferring the gel body (I) to a mould (II),
- casting a sol (II) containing zirconia crystallites so that it gets into contact with gel body (I), the zirconia crystallites having a crystal phase (2),
- transferring sol (II) into a gel body (II),
- optionally repeating steps (d) and (e) thereby casting additional sol(s) into either mould (II) or another mould to which the gel bodies of either step (d) or obtained after conducting step (e) have been transferred,
- removing solvent contained in the gel bodies to obtain an aerogel,
- heat-treating the aerogel to obtain a porous zirconia article.

The invention is also directed to a process of producing a dental ceramic article comprising the step of machining the porous dental milling block as described in the present text or the dental milling block obtainable by a process described in the present text and optionally sintering the dental ceramic article.

The invention is also directed to a kit of parts comprising at least one porous dental milling block as described in the present text or obtainable according to a process described in the present text, a treatment solution and optionally application equipment.

Definitions

The term "dental ceramic article" means any article which can or is to be used in the dental or orthodontic field, especially for producing of or as dental restoration, a tooth model and parts thereof.

Examples of dental articles include crowns, bridges, inlays, onlays, veneers, facings, copings, crown and bridged framework, implants, abutments, orthodontic appliances (e.g. brackets, buccal tubes, cleats and buttons) and parts thereof.

A dental article should not contain components which are detrimental to the patient's health and thus free of hazardous and toxic components being able to migrate out of the dental article.

The surface of a tooth is considered not to be a dental article.

By "dental milling block" is meant a solid block (3-dim article) of material from which a dental article, dental workpiece, dental support structure or dental restoration can or is to be machined. A dental milling block may have a size of about 20 mm to about 30 mm in two dimensions, for example may have a diameter in that range, and may be of a certain length in a third dimension. A block for making a single crown may have a length of about 15 mm to about 30 mm, and a block for making bridges may have a length of about 40 mm to about 80 mm. A typical size of a block as it is used for making a single crown has a diameter of about 24 mm and a length of about 19 mm. Further, a typical size of a block as it is used for making bridges has a diameter of about 24 mm and a length of about 58 mm. Besides the above mentioned dimensions, a dental milling block may also have the shape of a cube, a cylinder or a cuboid. Larger mill blocks may be advantageous if more than one crown or bridge should be manufactured out of one blank. For these cases, the diameter or length of a cylindric or cuboid shaped mill block may be in a range of about 100 to about 200 mm, with a thickness being in the range of about 10 to about 30 mm.

"Ceramic" means a non-metallic material that is produced by application of heat. Ceramics are usually hard, porous and brittle and, in contrast to glasses or glass ceramics, display an essentially purely crystalline structure. Ceramics are usually classified as inorganic materials.

"Crystalline" means a solid composed of atoms arranged in a pattern periodic in three dimensions (i.e., has long range crystal structure as determined by X-ray diffraction).

"Zirconia article" shall mean a 3-dimensional article wherein at least one the x,y,z dimension is at least about 5 mm, the article being comprised of at least about 80 or at least about 85 or at least about 90 or at least about 95 wt.-% zirconia.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and more traditional crystalline ceramics. It is formed as a glass, and then made to crystallize partly by heat treatment. Glass ceramics may refer to a mixture of lithium-, silicon-, and aluminium-oxides.

The porous ceramic dental material described in the present text does not contain a glass-ceramic.

"Sol" refers to a continuous liquid phase containing discrete particles having sizes in a range from 1 nm to 100 nm.

By "machining" is meant milling, grinding, cutting, carving, or shaping a material by a machine. Milling is usually faster and more cost effective than grinding. A "machinable article" is an article having a 3-dimensional shape and having sufficient strength to be machined.

A "powder" means a dry, bulk solid composed of a large number of fine particles that may flow freely when shaken or tilted.

A "crystallite" means a crystalline domain of a solid having a defined crystal structure. A crystallite can only have one crystal phase.

A "particle" means a substance being a solid having a shape which can be geometrically determined. The shape can be regular or irregular. Particles can typically be analysed with respect to e.g. grain size and grain size distribution. A particle can comprise one or more crystallites. Thus, a particle can comprise one or more crystal phases.

"Density" means the ratio of mass to volume of an object. The unit of density is typically g/cm$^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of a material sample can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" means a three-dimensional low density (e.g., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

A "green body" means an un-sintered ceramic item.

A "white body" means a pre-sintered ceramic item.

"Casting" means a manufacturing process by which a liquid material (e.g. solution or dispersion) is poured into a mould, which contains a hollow cavity of the desired shape, and then allowed to solidify.

A "geometrically defined article" means an article the shape of which can be described with geometrical terms including 2-dimensional terms like circle, square, rectangle, and 3-dimensional terms like layer, cube, cuboid, sphere.

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than about +/−5% or +/−2% or +/−1%.

"Ambient conditions" mean the conditions which the inventive solution is usually subjected to during storage and handling. Ambient conditions may, for example, be a pressure of about 900 to about 1100 mbar, a temperature of about 10 to about 40° C. and a relative humidity of about 10 to about 100%. In the laboratory ambient conditions are adjusted to about 20 to about 25° C. and about 1000 to about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

A material or composition is "essentially or substantially free of" a certain component within the meaning of the invention, if the material or composition does not contain said component as an essential feature. Thus, said component is not willfully added to the composition or material either as such or in combination with other components or ingredient of other components. A composition or material being essentially free of a certain component usually contains the component in an amount of less than about 1 wt.-% or less than about 0.1 wt.-% or less than about 0.01 wt.-% (or less than about 0.05 mol/l solvent or less than about 0.005 mol/l solvent or less than about 0.0005 mol/l solvent) with respect to the whole composition or material. Ideally the composition or material does not contain the said component at all. However, sometimes the presence of a small amount of the said component is not avoidable e.g. due to impurities.

Figure 1:
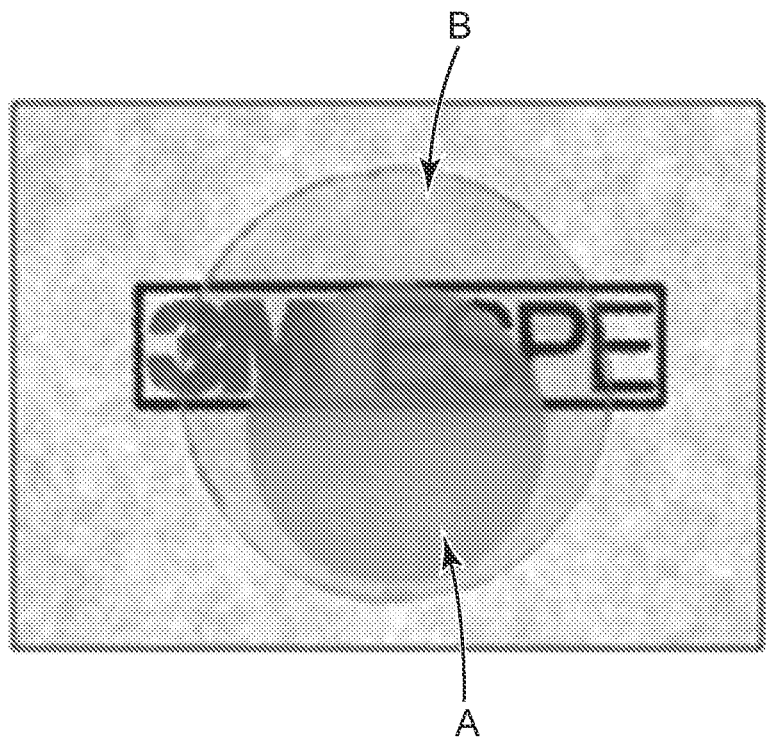
FIG. 1 shows a sintered zirconia disc comprising two sections of different translucency according to the invention.

It has been found that the porous zirconia dental mill block described in the present text fulfils the practitioners' needs especially with regard to the need for efficiently producing a dental article by a machining process.

The invention also facilitates the production of aesthetic dental articles, especially dental replacement parts without the need for a further (e.g. time consuming) veneering step, which is typically needed to mimic the appearance of a natural dental tooth.

Thus, the dental milling block described in the present text can be used for producing so-called monolithic dental articles.

The invention helps to address the problem which is often observed, if a ceramic material shall be provided comprising different sections, each section comprising a different ceramic having e.g. a different coefficient of thermal expansion. During a sintering process, the obtained ceramic material typically shows cracks or other defects.

The porous dental milling block described in the present text comprises at least two material sections, the material sections having different translucencies after sintering. The translucency of one material section (after sintering) is usually similar to the translucency of dentin (less translucent). The translucency of the other material section (after sintering) is usually similar to the translucency of enamel (more translucent).

A further positive aspect is that the less translucent part or material section has also a better toughness and/or hardness and/or strength (after sintering) compared to the more translucent part or material section. In addition, the more translucent part still has a better toughness and/or hardness and/or strength (after sintering) compared to conventional veneering materials, e.g. glass or glass ceramics.

Thus, the invention facilitates not only the production of highly aesthetic dental articles, but also dental articles having favourable physical parameters. The attributes profile of the dental milling block and the respective machined dental article (after sintering) described in the present text is similar to the attributes profile of a natural tooth with respect to translucency and/or toughness.

A natural tooth has also a less translucent internal section, a section which has to bear the load during chewing and a more translucent external section, a section which has a sufficient hardness to withstand the chewing forces.

However, the hardness of the outer section shall not be too high. Otherwise the dental replacement part may start damaging the sound dental hard tissue opposite to the dental replacement part during chewing.

The dental articles which can be machined out of the porous dental milling block described in the present text has thus a well balanced profile of attributes, e.g. adequate porosity before machining and/or coloring and sufficient hardness after sintering.

Further, as both material sections of the machined dental article are made from a material having a high toughness/hardness, the risk of chipping is reduced. Chipping may occur when using a less tough glass ceramic material as a veneering material for the dental article.

It was found that especially zirconia materials showing a $N_2$ adsorption and/or desorption of isotherm type IV (according to IUPAC classification) and/or a hysteresis loop (especially in a p/p0 range of 0.70 to 0.95) are suitable for producing a porous dental milling block.

Commercially available Y-TZP zirconia ceramic materials typically show a $N_2$ adsorption and/or desorption of isotherm type II (according IUPAC classification), which was found to be less effective if e.g. the translucency should be improved.

Materials showing a type II isotherm are said to be macro-porous, whereas materials showing a type IV isotherm are said to be meso-porous.

In contrast to the porous zirconia article described in the present text, zirconia materials described in the prior art do neither show a $N_2$ adsorption and desorption behaviour with a hysteresis loop nor a $N_2$ adsorption and/or desorption of isotherm type IV (according to IUPAC classification).

It was found that the zirconia crystallites having a cubic crystalline phase and the zirconia crystallites having a tetragonal crystalline phase as described in the present text can be sintered in a similar temperature range without major difficulties. This facilitates the co-firing of both materials.

Further, a material having meso-pores (and showing a type IV isotherm and/or hysteresis loop) can typically be machined more reliable than a material having macro-pores (and showing a type II isotherm), e.g. if the edge stability is taken into consideration.

If desired, the dental article obtained after machining the material described in the present text can be further individualized manually, e.g. using a file, a cutter or carving tool. The material (before sintering) is sufficiently hard to allow a precise machining but not too hard or too strong to prevent manually individualization.

In contrast to this, commercially available zirconia materials are often too soft and thus allow no precise carving or modelling in a pre-sintered stage.

The material described in the present text can also be easily and reliably be adapted to be reversibly fixed into a machining device. For example, this can be done by carving notches, recesses or grooves into the material.

Further, it was found that during the machining of the material of the porous dental mill block and/or during the manual individualization of the machined dental article described in the present text, less dust is produced, which may adhere to either the machining tools and/or the surface of the machined dental article.

In contrast to this, when machining a dental mill block of the state of the art it has been observed that various machine parts like suction grid, inner walls of milling chamber, frame holder are visibly covered with a thin layer of milling dust. In contrast to this, when machining the material of the dental milling block described in the present text the contamination of the machine parts with adhered milling dust is remarkably reduced.

Without wishing to be bound to a particular theory, it is believed that the favourable behaviour as regards the limited production of milling dust during milling can be related to its particle size distribution.

Unlike the milling dust obtained when machining milling blocks of the state of the art, the milling dust obtained when machining the material described in the present text shows a particle size distribution containing no or only a low fraction of particles smaller than 1 μm.

Further, it was found that during a manual adjustment or modification of the surface of the machined dental article, less milling dust adhered to the surface of the machined dental article when the material described in the present text was used (compared to using a material of the state of the art).

This will help to increase the productivity of the overall dental lab workflow since the often tedious cleaning steps needed to remove the adhered dust from the machined article (e.g. using brushes and/or pressurized air) can be reduced or are easier and faster to conduct.

The risk of failing to sufficiently remove the milling dust from the machined article—especially at the inner side of the dental restoration—combined with the risk to get a worse fit of the dental restoration to a prepared tooth surface is reduced.

Thus, using the material described in the present text will facilitate the production of high quality dental restoration(s).

The material described in the present text shows a variety of well balanced features (e.g. sufficient strength to be machined, adequate strength to be manually individualized, reduced wear of machining tools, desired translucency and/or reduced production of dust during machining).

Thus, the present invention facilitates the production of a dental ceramic article e.g. out of a monolithic block of zirconia material, the dental ceramic article (after sintering) having a material section (e.g. framework) containing a comparable high content of tetragonal phase containing zirconia material and a material section (e.g. surface region) containing a comparable high content of cubic phase containing zirconia material.

The porous dental milling block described in the present text comprises at least two Material Sections A and B.

Material Section A comprises zirconia crystallites having a tetragonal phase content A-T in % and a cubic phase content A-C in %.

Material Section B comprises zirconia crystallites having a cubic phase content B-C in % and a tetragonal phase content B-T in %.

The quotient of (tetragonal phase content A-T in %) to (cubic phase content A-C in %) in Section A is greater than 1. The greater this quotient is, the less transparent the material of Section A typically becomes.

The quotient of (tetragonal phase content B-T in %) to (cubic phase content B-C in %) in Section B is smaller than 1. The smaller this quotient is, the more transparent the material of Section B typically becomes.

According to one embodiment, the ratio of the tetragonal phase content A-T in % to the cubic phase content A-C in % in Material Section A is in a range from about 1.2 to about 50 or from about 1.5 to about 20.

According to another embodiment, the ratio of the tetragonal phase content A-T in % to the cubic phase content A-C in % in Material Section B is in a range from about 0.02 to about 0.8 or from about 0.05 to about 0.66.

The dental milling block described in the present text may comprise more than two material sections, e.g. 3, 4, 5 or 6 sections. The tetragonal phase content of the individual material sections may be same as or different from the tetragonal phase content of Material Sections A and B.

According to one embodiment, the porous material of the dental milling block described in the present text can typically be characterized by at least one of the following features as regards Material Section A and/or Material Section B before sintering the material to final density:

a) showing a N2 adsorption and/or desorption behaviour of isotherm IV according to IUPAC classification, b) showing a hysteresis loop when analyzed with regard to its adsorption and desorption behaviour to nitrogen;

c) showing a N2 adsorption and desorption behaviour with a hysteresis loop of type H1 according to IUPAC classification;

d) showing a N2 adsorption and desorption behaviour with a hysteresis loop in a p/p0 range of 0.70 to 0.95;

e) average connected pore diameter: from about 10 to about 100 nm or from about 10 to about 80 nm or from about 10 to about 50 nm;

f) average grain size of the zirconia crystallites: less than about 100 nm or less than about 80 nm or less than about 50 nm or less than about 30 nm;

g) BET surface: from about 10 to about 200 $m^2/g$;

h) Biaxial flexural strength: from about 10 to about 40 or from about 15 to about 30 MPa;

i) x, y, z dimension: at least about 5 mm or at least about 10 or at least about 20 mm;

j) Vickers hardness: from about 25 (HV 0.5) to about 150 (HV 1);

k) having an isotropic sintering behaviour;

l) density: 2.2 to 3.3 $g/cm^3$, m) sintering temperature: from about 1200 to about 1400° C.

If desired the above features can be determined as described in the Example section.

For Material Section A and/or Material Section B a combination of the following features can be preferred a, b, c, d, e, f and g, especially, if a dental milling block is desired with the following advantageous property: sintering temperature well below 1500° C.

For Material Section A and/or Material Section B a combination of the following features can be preferred h, I, j and l, especially, if a dental milling block is desired with the following advantageous property: good machinability.

Thus, the material of Section A or Section B might have essentially the same properties with respect to the parameters (a) to (m) described above, however, they differ with respect to the ratio of cubic to tetragonal crystalline phase content of the zirconia crystallites contained therein.

The porous zirconia material typically shows a N2 adsorption and/or desorption of isotherm type IV according to IUPAC classification.

It was found that material showing a N2 adsorption and/or desorption of isotherm type IV (according to IUPAC classification) and/or adsorption desorption isotherms with a hysteresis loop (especially in a $p/p_0$ range of 0.70 to 0.95) are particularly suitable.

The BET surface of porous zirconia materials described in the prior art is typically within a range from 2 to 9 $m^2/g$, whereas the BET surface of the porous zirconia materials described in the present text is preferably above 10 $m^2/g$.

The average grain size of the zirconia particles in the porous zirconia article described in the present text is small compared to the average grain size of the material of commercially available mill blanks.

A small grain size can be beneficial in that it typically leads to a more homogeneous material (from a chemical perspective), which may also result in more homogeneous physical properties.

Thus, the porous zirconia article described in the present text has a unique combination of features, which may facilitate a reliable production of highly aesthetic ceramic articles, especially with respect to edge stability.

It was found that it can be beneficial for certain properties, if the porous zirconia material has a certain average connected pore diameter. The average connected pore diameter should be in a particular range. It should not be too small and also not be too large.

The porous zirconia material described in the present text and used for providing the dental milling block has a smaller average connected pore diameter than porous zirconia ceramic material obtained by compacting zirconia powder, like 3Y-TZP powder (e.g. available from Tosoh Comp.).

Due to the nano-scaled particle size and specific average connected pore diameter of the material used for producing the porous zirconia ceramic material of the dental mill blank, this material has a different sintering behaviour compared to the zirconia ceramic material of dental mill blanks which are commercially available (e.g. LAVA™ Frame from 3M ESPE) and other zirconia ceramics available on the dental market being typically produced by compacting and pressing zirconia powder (e.g. 3Y-TZP zirconia powder from Tosoh Comp.).

The Vickers hardness of the material is typically also in a particular range.

If the Vickers hardness of the material is too low, the machinability could fall off in quality (edge chipping or breaking of the workpiece) as well as in the ease of manual reworking to individualize the frame of a dental restoration or a monolithic restoration as well.

If the Vickers hardness of the material is too high, the wear of the machining tools may increase in an uneconomic range or the tool could break and destroy the workpiece.

The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable efforts. The milling tool used or the milled material often tend to chip or break. In such a case the shaping of the material had to be done by grinding, e.g. using a Cerec™ grinding machine (Sirona).

According to a particular embodiment the porous zirconia material can be characterized by the following features:
  showing a N2 adsorption of isotherm type IV according to IUPAC classification,
  showing a N2 adsorption with a hysteresis loop in a p/p0 range of 0.70 to 0.95,
  average connected pore diameter: from about 15 to about 60,
  average grain size: less than about 100 nm,
  BET surface: from about 15 to about 100 $m^2/g$ or from about 16 to about 60 $m^2/g$,
  Biaxial flexural strength: from about 10 to about 40 MPa,
  x, y, z dimension: at least about 5 mm,
  Vickers hardness: from about 25 (HV 0.5) to about 150 (HV 1);
  Density: from about 40% to about 60% of theoretical density.

The dental milling block typically has dimensions suitable to be machined by a machining device.

The porous dental milling block may have the shape of a disc or block (e.g. cuboid, cylinder).

Useful ranges for the x, y and z dimensions of the dental milling block include from about 5 to about 300 or from about 8 to about 200 mm.

Material Sections A and B of the dental milling block described in the present text are geometrically defined.

The geometrically defined sections may have the shape of layers (e.g. flat, convex or concave) or blocks, which may be arranged e.g. in a stacked or core-shell structure, or may have tooth-like shapes, e.g. defining a dentin and an enamel section.

Figure 3:
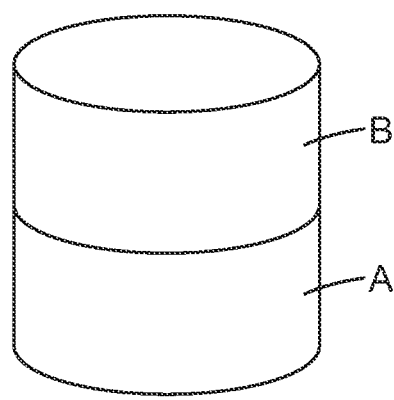
FIG. 3 shows an embodiment of a dental milling block with two sections, wherein the sections are arranged as layers.
Figure 4:
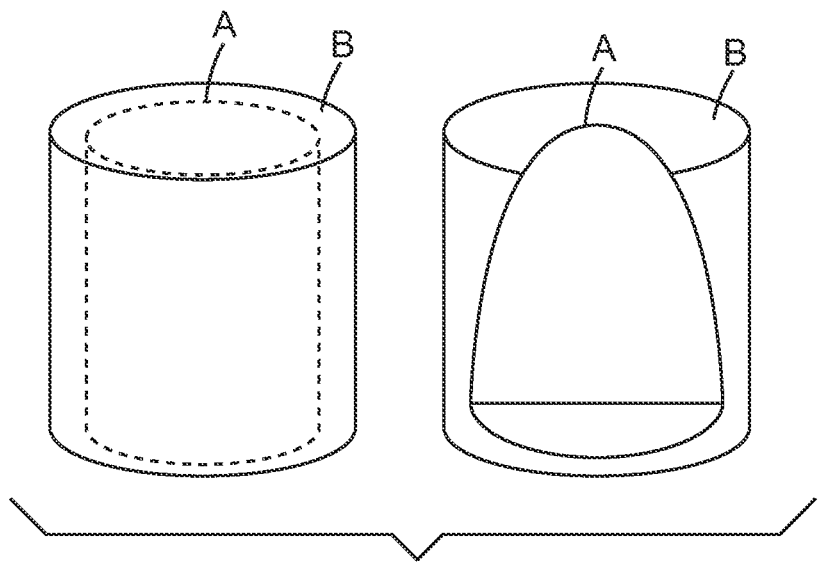
FIG. 4 shows two embodiments of a dental milling block with two sections, wherein the sections are arranged in a core-shell structure.

Examples of dental milling blocks are shown in FIG. 3 and FIG. 4. FIG. 3 shows a dental milling block comprising two sections A and B arranged in a layered structure. FIG. 4 shows two possibilities for a dental milling block, wherein sections A and B are arranged in a core-shell structure.

The porous dental milling block typically comprises means for attaching the block to a machining device, especially to the clamping appliance(s) of such a device.

Suitable means include groove(s), recesse(s), notche(s), stamp(s) and combinations thereof.

In another embodiment, the dental milling block is fixed to or contained in a holding device. The holding device containing the dental milling block may then function as a means for attaching the blank to a machining device.

Fixing of the dental milling block to a holding device can be effected by clamping, gluing, screwing and combinations thereof.

Useful holding devices include frames (open and closed) or stumps.

Using a holding device may facilitate the production of the dental article with a machining device.

Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

According to one embodiment, the dental milling block described in the present text can typically be characterized by at least one of the following features as regards the porous material of Section A and/or Section B before sintering to final density:
  ZrO2 content: from about 70 to about 98 mol % or from about 80 to about 97 mol %;
  HfO2 content: from about 0 to about 3 mol % or from about 0 to about 2 mol % or from about 0.1 to about 1.8 mol %;
  Y2O3 content: from about 1 to about 15 mol % or from about 1.5 to about 10 mol % or from about 2 to about 5 mol %;
  Al2O3 content: from about 0 to about 1 mol % or from about 0.005 to about 0.5 mol % or from about 0.01 to about 0.1 mol %.

According to one embodiment, the dental milling block described in the present text can be characterized by the following features:
  Material Section A (before sintering) showing a N2 adsorption of isotherm type IV according to IUPAC classification and having a BET surface from about 10 to about 200 $m^2/g$,
  Material Section B (before sintering) showing a N2 adsorption of isotherm type IV according to IUPAC classification and having a BET surface from about 10 to about 200 $m^2/g$.

It was found that a higher Y2O3 content typically leads to an increase of the cubic crystal phase in the zirconia ceramic material after having sintered the material to final density. A higher content of the cubic crystal phase may contribute to a better translucency.

The dental milling block described in the present text does typically not comprise oxides selected from TiO2, SiO2 or mixtures thereof in an amount above 2 mol % or above 1 mol % or above 0.5 mol % or above 0.3 mol % or above 0.1 mol %, mol % with respect to the weight of the ceramic material the dental milling block is made of.

The invention is also directed to processes of producing the porous dental milling block described in the present text.

According to one embodiment, the porous dental milling block can be produced by a process comprising the following steps:
  a) casting a sol (I) containing zirconia crystallites into a mould (I), the zirconia crystallites having a crystal phase (1),
  b) transferring the sol (I) to a gel body (I),
  c) optionally transferring the gel body (I) to a mould (II),
  d) casting a sol (II) containing zirconia crystallites so that it gets into contact with gel body (I), the zirconia crystallites having a crystal phase (2),
  e) transferring sol (II) into a gel body (II),
  f) optionally repeating steps (d) and (e) thereby casting additional sol(s) (e.g. sol (III), sol (IV), sol (V), etc.) into either mould (II) or another mould (e.g. mould (III), mould (IV), mould (V), etc.) to which the gel bodies of either step (d) or obtained after conducting step (f) have been transferred,
  g) removing the solvent contained in the gel bodies to obtain an aerogel,
  h) heat-treating the aerogel to obtain a porous zirconia article.

The process described in the present text enables the skilled person to provide a porous zirconia article e.g. in the shape of a porous dental milling block comprising at least two material sections having different concentrations of zirconia crystallites, the zirconia crystallites having certain crystal phases (1) and (2).

The crystal phases (1) and (2) comprise the cubic and tetragonal phase.

Besides the cubic and tetragonal phases, the zirconia crystallites may also comprise small amounts (e.g. below about 5, 4, 3, 2 or 1 wt.-%) of a monoclinic phase.

Such an article can be machined, if desired, and finally sintered.

The transfer of the sol into a gel body can be accomplished by methods known to the skilled person.

The means for effecting such a transfer depends from the nature of the sol(s) used.

One method involves the use of a polymerizable material (e.g. the use of a (meth)acrylate) which can be polymerized to a polymer containing the zirconia crystallites.

Despite the fact that the zirconia article comprises two different crystal phases which typically require a different sintering temperature due to the different coefficient of thermal expansion inherent to a zirconia material having a certain crystal phase, it has surprisingly been observed that the zirconia article can be sintered at a certain sintering temperature to a sintered zirconia article not showing visible (e.g. to the human eye) cracks or defects.

This enables the skilled person to provide e.g. a porous dental milling block comprising a material section (A) comprising mainly zirconia crystallites having a tetragonal crystal phase and a material section (B) comprising mainly zirconia crystallites having a cubic crystal phase.

Such a dental milling block can be machined and the machined zirconia material sintered.

The sintered machined zirconia material will still comprise two material sections (A) and (B), differing from each other with respect to translucency and strength.

The material section (A)—comprising mainly zirconia having a tetragonal crystal phase—has a high strength but a low translucency.

In contrast to this, the material section (B)—comprising mainly zirconia having a cubic crystal phase—has a lower strength but a higher translucency compared with material section (A).

In the dental area, material section (A) may function as a kind of framework (e.g. load bearing part of a dental restoration), whereas material section (B) may function as a kind of facing or veneer (e.g. aesthetic part of a dental restoration).

The dental article described in the present text can be obtained by conducting one or more of the following process steps:
  1. Casting a first zirconia sol in a mould (I) with a desired shape, e. g. conical, cylindrical or dentin core-like structure and curing the sol to a gel body.
  2. Transferring the gel body to a bigger mould (II). The bigger mould (II) may have the same shape as the mould (I) or a different shape.
  3. Applying a second zirconia sol (if desired, with an adjusted density and a different translucency grade compared to the first zirconia sol) in the mould (II). Curing the second zirconia sol to a gel body.
  4. If desired, repeating steps 2 and 3 according to the number and structure or shape of layers desired.
  5. If desired, conducting a solvent exchange process.
  6. If desired, conducting a supercritical extraction step.
  7. If desired, conducting a heat-treatment step to remove organic material (e.g. binder) if present.
  8. Pre-sintering the composition to obtain a pre-sintered article having sufficient strength for conducting a machining step.

According to another embodiment or an embodiment describing the above described process more precisely, the porous dental milling block can be produced by a process comprising the following steps:
  providing a Mixture A of a Sol S1-T and a Sol S2-C,
    Sol S1-T comprising tetragonal zirconia crystallites,
    Sol S2-C comprising cubic zirconia crystallites,
    the amount of tetragonal zirconia crystallites in Sol S1-T in wt.-% being greater than the amount of cubic zirconia crystallites in Sol S2-C in wt.-%
    the mixture further comprising a polymerizable system containing polymerizable component(s) and initiator component(s),
  providing a Mixture B of a Sol S2-T and a Sol S2-C,
    Sol S2-T comprising tetragonal zirconia crystallites,
    Sol S2-C comprising cubic zirconia crystallites,
    the amount of tetragonal zirconia crystallites in Sol S2-T in wt.-% being smaller than the amount of cubic zirconia crystallites in Sol S2-C in wt.-%
    the mixture further comprising a polymerizable system containing polymerizable component(s) and initiator component(s),
  conducting one of the following steps:
    optionally curing Mixture A to obtain a dental milling block precursor A or,
    optionally curing Mixture B to obtain a dental milling block precursor B,
  bringing into contact
    if present, Mixture A with Mixture B or
    if present, dental milling block precursor A with Mixture B or
    if present dental milling block precursor B with Mixture A to obtain System AB,
  curing System AB to obtain a dental milling block precursor AB,
  if present, removing remaining solvent,
  heating the dental milling block precursor AB to a temperature where the components of the polymerizable system or polymerized system pyrolyse.

The process may also contain the following steps:
providing a Sol S1-T comprising tetragonal zirconia crystallites,
providing a Sol S1-C comprising cubic zirconia crystallites,
the amount of tetragonal zirconia crystallites in Sol S1-T in wt.-% being greater than the amount of cubic zirconia crystallites in Sol S1-C in wt.-%,
mixing Sol S1-T and Sol S1-C to obtain a Mixture A,
adding a polymerizable system containing polymerizable component(s) and initiator component(s) to Mixture A,
casting the mixture into a mould,
optionally curing the mixture to obtain a dental milling block precursor A,
providing a Sol S2-T comprising tetragonal zirconia crystallites having a tetragonal phase content,
providing a Sol S2-C comprising cubic zirconia crystallites having a cubic phase content,
the amount of tetragonal zirconia crystallites in Sol S2-T in wt.-% being smaller than the amount of cubic zirconia crystallites in Sol S2-C in wt.-%,
mixing Sol S2-T and Sol S2-C to obtain a Mixture B,
adding a polymerizable system containing polymerizable component(s) and initiator component(s) to Mixture B,
bringing the dental milling block precursor A in contact with Mixture B to obtain System AB,
drying System AB to obtain a dental milling block precursor AB,
if present, removing remaining solvent,
heating the dental milling block precursor AB to a temperature where the components of the polymerisable system or polymerized system pyrolyse.

According to another embodiment or an embodiment describing the above described process(es) more precisely, the porous dental milling block can be produced by a process comprising the following steps:
providing a Sol A,
Sol A comprising tetragonal zirconia crystallites in an amount A-T in wt.-% and cubic zirconia crystallites in an amount A-C in wt.-%,
the amount of tetragonal zirconia crystallites of Sol A being greater than the amount of cubic zirconia crystallites in Sol A,
Sol A further comprising a polymerizable system containing polymerizable component(s) and initiator component(s),
providing a Sol B,
Sol B comprising tetragonal zirconia crystallites in an amount B-T in wt.-% and cubic zirconia crystallites in an amount B-C in wt.-%,
the amount of tetragonal zirconia crystallites of Sol B being smaller than the amount of cubic zirconia crystallites in Sol B,
Sol B further comprising a polymerizable system containing polymerizable component(s) and initiator component(s),
conducting one of the following steps:
optionally curing Sol A to obtain a dental milling block precursor A,
optionally curing Sol B to obtain a dental milling block precursor B,
bringing into contact
if present, Sol A with Sol B or
if present, dental milling block precursor A with Sol B or
if present, dental milling block precursor B with Sol A
to obtain System AB,
curing System AB to obtain a dental milling block precursor AB,
if present, removing remaining solvent,
heating the dental milling block precursor AB to a temperature where the components of the polymerizable system or polymerized system pyrolyse.

The process of producing the porous ceramic zirconia material typically starts with providing a sol comprising zirconia crystallites having a certain tetragonal phase content and a sol comprising zirconia crystallites having a certain cubic phase content.

These kinds of sols can generally be produced e.g. by hydrothermal treatment of an aqueous metal salt solution or suspension (e.g. zirconium salt, yttrium salt).

More precisely, a precursor solution is prepared by combining a zirconium salt (e.g. acetate) solution and a solvent (e.g. water). A phase stabilizing agent (e.g. yttrium acetate) is added and dissolved in the precursor solution. The resulting composition is pumped e.g. through a hydrothermal reactor.

When subjected to hydrothermal treatment, the various dissolved salts undergo hydrolysis and condensation reactions to form zirconia-based particles. These reactions are often accompanied with the release of an acidic byproduct (e.g. acetic acid).

Suitable hydrothermal reactors are described e.g. in U.S. Pat. No. 5,453,262 (Dawson et al.) and U.S. Pat. No. 5,652,192 (Matson et al.).

A more detailed description can be found e.g. in EP application no. 12179125.5 on page 15, line 19 to page 23, line 7. This text is herewith incorporated by reference.

The content of tetragonal and/or cubic phase of the zirconia crystallites can be adjusted by varying the amount of phase stabilizing components added during the production method.

Phase stabilizing components which can be used include Ce, Mg, Ca, Y, rare earth elements and combinations thereof.

A more detailed description can be found in U.S. application 61/545,243 (3M IPC) and EP application 12179125.5 (3M IPC) filed on Aug. 3, 2012. The content of these references is herewith incorporated by reference.

The sols can be mixed in order to adjust the ratio of cubic to tetragonal phase content of the zirconia crystallites contained therein further, if desired.

To the sol of $ZrO_2$ particles a surface-modifying agent is typically added, preferably a polymerizable surface-modifying agent (e.g. a radically reactive surface modifier).

The $ZrO_2$ particles having been surface-modified with a polymerizable agent can be polymerized, if desired, to provide a composition comprising crosslinked $ZrO_2$ particles.

The polymerizable surface-modifying agent can be removed later, e.g. during a calcining and/or pre-sintering step.

If desired, the sol is casted into a mould. The mould may have the negative shape of the dental mill block to be provided. Due to size reduction which may be caused by heat treatments of the material, the size of the mould is typically larger than the size of the final dental mill blank.

The shape of the mould is not particularly limited.

The casted zirconia sol can be treated with heat or radiation in order to start polymerization of the reactive surface modifier. This process usually results in a gel.

If present and desired, solvent (e.g. water) may be removed from the gel, at least partially.

Remaining solvent of the above described sol/gel process can be removed, e.g. by supercritical extraction techniques resulting in an aerogel (e.g. in block form).

If desired, the obtained aerogel may be cut into smaller pieces.

The process for producing the porous dental milling block described in the present text is beneficial in that it reduces the risk that the previous and optionally cured layer of material re-disperses during the following cast and cure step. Such a re-dispersion could result in a not desired un-defined mixture, which may result in defects during a later sintering process or at least in an undefined distribution of translucency and toughness throughout the milling block.

According to a further embodiment, Material Section A and/or Material Section B of the dental milling block precursor AB can be characterized by at least one of the following features:

a. comprising crystalline zirconia particles (with tetragonal or cubic phase) having an average primary particle size in a range from 2 nm to 50 nm or from about 2 nm to about 30 nm or from about 2 to about 20 or from about 2 to about 15 nm;

b. content of zirconia in the particles: at least about 85 mol-%;

c. having an organic content of at least 3 wt.-% or within a range from about 3 to about 10 wt.-% (before application of the heating step resulting in a pyrolysis of the organic material);

d. x, y, z dimension: at least about 5 or at least about 8 or at least about 10 or at least about 20 mm.

A combination of the features (a) and (b) or (a) and (c) or (a), (b) and (c) can be preferred.

A thickness of the Material Sections A and/or B of at least about 5 or at least about 8 or at least about 10 or at least about 20 mm allows for shaping the respective section e.g. by a milling process.

The heat treatment for obtaining the dental milling block precursor is typically done under the following conditions:

temperature: from about 900 to about 1100° C. or from about 950 to about 1090° C.; from about 975 to about 1080° C.;

atmosphere: air or inert gas (e.g. nitrogen, argon);

duration: until a density of about 40 to about 60% of the final density of the material has been reached.

The heat treatment or calcining can be conducted in one or more steps.

In a first heat treatment step a binder burn-out could be performed to remove all organic additives from previous process steps to obtain a so called "white body".

In a second heat treatment step the strength and/or the hardness of the white-body could be adjusted to the needs of the follow up processes like machining. In case of a machinable blank the sintering protocol should reflect the interaction of temperature with strength and/or hardness.

If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

Adjusting the dwell time (that is the time during which the aerogel is kept at a certain temperature) can be helpful as well. Adjusting the dwell time may facilitate tuning the strength and/or hardness to the specific needs of the chosen machining technology. The dwell time can be in a range from about 0 to about 24 h or from about 0.1 to about 5 h.

If the dwell time is too long, the dental mill blanks may become too hard to be machined under reasonable conditions.

The process of producing a dental article may further comprise the step of machining the porous dental milling block as described in the present text to obtain a machined dental article.

If desired, the dental article can also be produced using a so-called free form shaping technique instead of simply machining the dental article out of a block.

The practitioner can use a computer system and virtually arrange the desired dental article in the multi-sectional dental milling block described in the present text in such a way, that the desired translucency distribution of the dental restoration mimics the appearance of a natural tooth.

The algorithm of such a process is known to the practitioner from different commercially available grinding systems using multi-layered glass ceramic materials (e.g. Cerec software; Sirona company).

The machined dental article can optionally be sintered to obtain a dental ceramic article.

The heat treatment for obtaining the sintered dental ceramic article is typically done under the following conditions:

temperature: from about 1100 to about 1500° C. or from about 1200 to about 1400° C. or from about 1250 to about 1350° C. or from about 1200 to about 1400° or from above about 1300 to about 1400° C. or above about 1320° C. to about 1400° C. or above about 1340° C. or above about 1350° C.;

atmosphere: air or inert gas (e.g. nitrogen, argon);

pressure: ambient pressure;

duration: until a density of about 95 to about 100% of the final density of the material has been reached.

The dwell time (that is the time during which the article is kept at that temperature) can be zero. The dwell time, however, can also be in a range from about 0 to about 24 h or from about 0.1 to about 5 h.

The invention is also directed to a dental article obtainable or obtained by the processes described in the present text.

The dental article may have the shape of a crown, bridge, inlay, onlay, veneer, facing, coping, crown and bridged framework, implant, abutment, orthodontic appliances (e.g. brackets, buccal tubes, cleats and buttons) and parts thereof.

The dental article (after machining but before conducting a sintering step) has sufficient open porosity to take up (i.e. absorb) liquids or solutions, if desired.

According to one embodiment the dental ceramic article (after sintering) described in the present text can be further characterized by at least one of the following features:

a) comprising at least two Sections A and B with different translucencies;

b) phase content tetragonal phase of Material Section A: from about 50 to about 100 wt.-% or from about 60 to about 100 wt.-%;

c) phase content cubic phase of Material Section A: from about 0 to about 50 wt.-% or from about 0 to about 40 wt.-%;

d) phase content tetragonal phase of Material Section B: from about 0 to about 50 wt.-% or from about 10 to about 50 wt.-%;

e) phase content cubic phase of Material Section B: from about 50 to about 100 wt.-% or from about 50 to about 90 wt.-%;

f) density: at least about 98.5 (in some embodiments, 99, 99.5, 99.9, or even at least 99.99) percent of theoretical density g) biaxial flexural strength: from about 450 MPa to about 2200 MPa, or from about 500 MPa to about 2000 MPa (determined according to ISO 6872);

h) CR-R value (contrast ratio reflectance) of Material Section A: from about 40 to about 90%;

i) CR-R value (contrast ratio reflectance) of Material Section B: from about 5 to about 40%.

If desired the above features can be determined as described in the Example section.

A combination of the features a, b, c, d and e or h and i can sometimes be preferred especially if a high aesthetic dental article is desired.

The invention is also directed to a kit of parts comprising at least one porous dental milling block as described in the present text or obtainable according to a process described in the present text, treatment solution(s) and optionally application equipment.

A suitable treatment solution typically contains a solvent and certain ions.

The solvent is able to dissolve the ion(s) contained in the treatment solution. If desired, mixtures of different solvents can be used.

Suitable solvents include water, alcohols (especially low-boiling alcohols, e.g. with a boiling point below about 100° C.) and ketons.

The solvent should be able to dissolve the coloring ions used.

Specific examples of solvents which can be used for dissolving the cations of the non-colouring agent include water, methanol, ethanol, iso-propanol, n-propanol, butanol, acetone, and mixtures thereof.

The solvent is typically present in an amount from about 50 to about 99.9 wt.-% or from about 60 to about 99 wt.-% or from about 75 to about 95 wt.-%, wt.-% with respect to the whole solution.

The treatment solution has typically an adequate viscosity so that a sufficient amount of solution can not only be applied to the surface of the porous zirconia article but also is able to migrate into the pores of the zirconia article.

Adjusting the viscosity to a value as indicated above can be beneficial in that the solution can be more accurately applied to particular sections or regions of the porous dental zirconia article obtained after machining the porous dental milling block.

If the viscosity of the treatment solution is too high, the solution might not be able to sufficiently enter the pores of the zirconia material. On the other hand, if the viscosity of the solution is too low, the solution might migrate into the pores too rapidly and might diffuse into the whole article.

In a further embodiment the solution is transparent.

The treatment solution may contain coloring ions.

According to one embodiment, the treatment solution comprises coloring ions selected from ions of Fe, Mn, Er, Pr, Tb, V, Cr, Co, Mo and mixtures thereof.

After firing the machined dental zirconia article (e.g. to final density), the presence of the coloring ions will result in an at least partially colored dental zirconia article.

The solution may contain phase stabilizers including ions of Y, Ce, Mg, Ca, rare earth elements and mixtures thereof. The addition of phase stabilizers may further facilitate the stabilization of a certain crystalline phase (e.g. cubic or tetragonal phase).

The solution may also contain on or more complexing agent(s).

The complexing agent(s) may support the penetration of the coloring solution.

Adding a complexing agent can be beneficial to improve the storage stability of the solution, accelerate the dissolving process of salts added to the solution and/or increase the amount of salts which can be dissolved in the solution.

The complexing agent is typically able to form a complex with the metal ions being present in the solution. The complex formed should be soluble in the solvent. Typically the complex formed is better soluble in the solvent than in water.

E.g., the complexing agent can be used in an at least stoichiometric ratio with respect to the molar amount of the ions contained in the effect agent.

Good results can be achieved, if the molar ratio of the complexing agent to the cations of the non-coloring agent is equal to or greater than about 1 or about 2 or about 3.

If the amount of complexing agent used is too low, the non-colouring agent might not be dissolved entirely.

If the amount of complexing agent used is too high, the excess complexing agent itself might remain unsolved.

The complexing agent is usually added as a separate component of the solution.

However, it can also be added or be present in form of an anion of the agent to be brought into solution.

Examples include acetylacetonate, crown ethers, cryptands, ethylenediaminetriacetate and its salts, ethylene diamine tetraacetate and its salts, nitrilotriacetate and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts and mixtures thereof.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

Typically, the complexing agent is present in the solution in an amount sufficient to dissolve at least the cations of the coloring agent in the solvent or to prevent precipitation of these cations.

The complexing agent can be present in an amount of at least about 1 wt.-% or at least about 5 wt.-% or at least about 10 wt.-% with respect to the amount of the whole composition. There is no upper limit, however, usually the amount of complexing agent used does not exceed an amount of about 50 wt.-% or about 40 wt.-% or about 30 wt.-% with respect to the amount of the whole solution.

The solution may also contain one or more thickening agent(s).

The thickening agent(s) may help to adjust the viscosity of the treatment solution and thus contribute to control the depth of penetration and spreading of the treatment solution once applied to the surface of the porous zirconia article.

Typically, the thickening agent(s) can be characterized by at least one of the following features:

viscosity: from about 1 to about 2,000 mPa*s or from about 100 to about 1,500 mPa*s (measured at 23° C. at a shear rate of 50 s-1);

free of polymerizable groups like (meth)acrylate groups, epoxy groups, carbon-carbon unsaturated groups;

not containing elements like S, P.

Thickening agent(s) which can be used include polyol(s) (including polyvinyl alcohol), glycol ether(s) (e.g. PEG 200, PEG 400, PEG 600, diethylene glycol methyl ether, diethylene glycol ethyl ether), di- and polyalcohol(s) (including 1,2-propanediol, 1,3-propanediol, glycerol), glycerol ether, polysaccharide(s), xanthan gum, methyl cellulose and mixtures thereof.

Polyethylene glycols which can be used can be represented by formula (1)

$$R1O\text{---}(CH2\text{-}CH2\text{-}O)m\text{-}R1 \qquad (1)$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and m=about 2 to about 100, preferably about 2 to about 20, more preferably about 2 to about 5

The average molecular weight (Mw) of the polyethylene glycol should be in the range of about 100 to about 500,000, preferably in the range of about 1,000 to about 100,000, more preferably in the range of about 1,000 to about 50,000.

If present, the thickening agent is typically present in the following amount: from about 1 to about 15 wt.-% or from about 2 to about 10 wt.-% or from about 3 to about 8 wt.-% with respect to the whole solution.

The treatment solution may also contain marker substance(s).

Adding a marker substance(s) can be beneficial in order to enhance the visibility of the treatment solution during use, especially, if the solution is transparent. Thus, the practitioner can easily determine to which parts of the surface of the zirconia article the treatment solution has already been applied and which parts have not been treated yet and should remain untreated. On the other hand, if the marker substance is an organic substance, the marker substance(s) will be burnt during a later sintering step and thus not be incorporated into the crystal structure of the zirconia article.

Examples of marker substance(s) which can be used include food colorants like Riboflavin (E101), Ponceau 4R (E124), Green S (E142).

If present, the marker substance is typically present in the following amount: from about 0.0001 to about 5 wt.-% or from about 0.001 to about 3 wt.-% or from about 0.01 to about 1 wt.-% with respect to the whole treatment solution.

The treatment solution may also contain one or more additive(s).

Additives which can be added to the solution include stabilizers (such as methoxy phenol hydrochinone, Topanol A, and mixtures thereof), buffers (such as acetate or amino buffers and mixtures thereof), preservative agents (such as sorbic acid or benzoic acid and mixtures thereof) and mixtures thereof.

There is no need for additive(s) to be present, however, if they are present, they are typically present in an amount which is not detrimental to the purpose to be achieved when applying the solution.

If additive(s) are present, they are typically present in an amount of about 0.01 to about 10 wt.-% or from about 0.05 to about 5 wt.-% or from about 0.1 to about 3 wt.-% with respect to the whole treatment solution.

The treatment solution does typically not comprise at least of the following components solid particles settling from the solution upon storage for more than about 2 hours.

The treatment solution does typically also not comprise solid particles which may or will remain on the surface of a zirconia article once the solution is applied to the surface of the zirconia article.

Thus, the treatment solution described in the present text is neither a dispersion of solid particles in a solvent nor a slurry.

According to a further embodiment, the treatment solution comprises the components in the following amount:
cations of coloring agent(s) in an amount of about 0.1 to about 5 wt.-% or from about 0.1 to about 4 mol-%,
cations of phase stabilizing agent(s) in an amount of about 0.1 to about 5 wt.-% or from about 0.1 to about 4 mol-%,
solvent in an amount of about 50 to about 99 wt.-% or from about 60 to about 98 wt.-%,
optionally complexing agent(s) in an amount of about 1 to about 50 wt.-% or from about 5 to about 40 wt.-%,
optionally thickening agent(s) in an amount of about 1 to about 15 wt.-% or from about 2 to about 10 wt.-%,
optionally organic marker substance(s) in an amount of about 0.0001 to about 5 wt.-% or from about 0.001 to about 3 wt.-%,
optionally additives in an amount of about 0.01 to about 10 wt.-% or from about 0.05 to about 5 wt.-%,
wt.-% with respect to the whole composition.

The treatment solution can be produced by mixing its components. This can be done at room temperature or by applying heat and/or while stirring. Applying heat and/or stirring can be beneficial in order to accelerate the dissolution process of the effect agent into the solvent. The composition is typically stirred until the ions are completely dissolved in the solvent. If desired, additives (like those mentioned above) can be added. Undesired precipitations can be removed by filtering, if desired.

Examples of coloring solutions which can be used are described e.g. in U.S. Pat. No. 6,709,694, US 2006/0117989, WO 2009/014903 or EP application No. 1177189. The content of these documents is herewith incorporated by reference.

Examples of application equipment which can be included in the kit of parts described in the present text include brushes, sponges, (hollow) needles, pens, mixing appliances and combinations thereof.

Examples of mixing appliances include mixing wells, trays, plates and slides.

According to one embodiment the treatment solution described above is applied to the surface of the zirconia article with a pen, the pen comprising a housing, a brush tip, a removable cap and a reservoir for storing the non-water based solution described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the treatment solution and will help the practitioner to save time.

Currently, coloring solutions are usually offered in bottles and are applied to porous ceramics with a separate brush or even by dipping the entire ceramic into the coloring solution. This often goes along with a lot of waste of the coloring solution. By using a pen, there will be essentially no waste of the coloring solution.

Further, a pen with a cap will prevent the pen from drying out if not used.

Providing individual pens for individual treatment solutions may further facilitate the application of the composition to the surface of porous dental ceramic(s). Until now, usually only one brush is used and that brush has to be cleaned thoroughly before a further coloring solution is applied.

If, however, one pen for one color is provided, switching the colors during the application process is quite easy and more save for the dental technician, while mixing of different colors using this kind of equipment is still possible by subsequent application of different colors to the ceramic surface.

The volume of the reservoir may be in a range from about 1 ml to about 10 ml or from about 2 ml to about 5 ml.

The reservoir may be removable or fixed to the housing of the pen.

According to one embodiment, the reservoir is exchangeable. The exchangeable reservoir may have the shape of a cartridge or bullet.

The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from about 5 to about 20 mm or from about 8 to about 15 mm. If the bristles are too short, application of the solution to the inside of a dental restoration may be difficult. If, on the other hand, the bristles are too long, the handling of the brush itself might become impractical for dental applications.

The thickness of the brush tip at its base is typically in the range from about 0.3 to about 5 mm or from about 1 to about 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the solution properly, that is either too little to too much of the solution is applied. Both may be detrimental for achieving an accurately colored dental ceramic.

The shape of the brush tip should be tapered and fan out, if desired, when pressure is applied. Thus, the brush tip should have some flexibility. A brush tip with these properties can be used to draw thin lines and also to paint on larger areas.

A combination of a brush tip comprising bristles having a length from about 8 to about 15 mm and the coloring solution described in the present text having a viscosity above about 200 mPa*s or above about 500 mPa*s (measured at 23° C.) was found to be beneficial. Such a combination facilitates the accurate application of the treatment solution on the surface of the porous dental ceramic article.

If desired, the treatment solution can applied to only certain sections of the surface of the zirconia dental article. That is, the treatment solution is only applied to parts of the surface of the article but not to the whole surface.

Alternatively, the treatment solution can be applied to the whole surface of the zirconia dental article. In this respect, the dental zirconia dental article is dipped into the treatment solution.

Moreover, the treatment solution cannot only be applied to dry surfaces of zirconia dental articles, but also to wetted surfaces, especially to pre-sintered zirconia dental articles.

Selectively applying the treatment solution to the surface of the porous zirconia dental article is usually achieved by painting e.g. using a brush. However, the treatment solution can also be applied by using a sponge, a fabric, brush-pen or by spraying, equipment which is described in more detail above.

Drying the treated zirconia article is not absolute necessary, but can be preferred to reduce the time needed for firing and to avoid undesired in-homogenous color effects. Drying can be effected by simply storing the zirconia article e.g. on a plate at ambient conditions for a couple of hours (about 1 to about 3 h). If, however, a high boiling solvent is used, drying might be difficult to achieve.

The dental articles described in the present text do typically not contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-colored article are usually not contained in the final dental restoration. Typically, an article is characterized as tooth colored if it can be allocated a color from the Vita™ color code system, known to the person skilled in the art.

Moreover, if possible, the dental milling block should not or only contain ingredients which can be detrimental to the firing equipment used during the sintering process.

According to a further embodiment, the dental milling block does not contain glass or glass/ceramic particles.

The producing of the zirconia material does typically also not require the application of a hot isostatic pressing step (HIP).

The complete disclosures of the patents, patent documents, and publications cited herein are incorporated by reference in their entirety as if each were individually incorporated.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements

Crystalline Phase Content

The phase content can be determined by x-ray defraction (XRD) using a BrukerD8 Discover device (Bruker AXS) and the TOPAS™ software provided by the manufacturer (Bruker) applying the Rietveld analyses and using the Bragg-Brentano geometry.

The content of the following phases was determined: cubic and tetragonal.

The phase content calculated by the TOPAS™ software is given in wt.-%.

The measurement is typically performed down to a depth of 3 to 6 μm.

pH-Value

If desired, the measurement of the pH-value can be achieved by means known by the person skilled in art. E.g. an instrument like Metrohm™ 826 or pH indicator paper can be used.

Viscosity

If desired, the measurement can be done as follows:

A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to $50\ s^{-1}$. The measurement is done 500 s after starting the shearing process of the composition.

Method for Measuring N2 Sorption Isotherms, BET Surface Area, Pore Volume, Average Connected Pore Diameter If desired, the measurement can be done as follows:

The samples are run on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples are weighed and outgassed at 200° C. for two days then subjected to a N2 sorption process with an appropriate number and distribution of measurement points, e.g. 55 adsorb points and 20 desorb points from a $P/P_o$, range $1 \times 10^6$ to 1 and back to 0.05 giving full isotherms. The specific surface area S is calculated by the BET method (Details regarding calculation see Autosorb-1 Operating Manual Ver. 1.51 IV. Theory and Discussion, Quantachrome Instruments, Inc.). The total pore volume $V_{liq}$ is derived from the amount of vapor adsorbed at a relative pressure close to unity ($P/P_o$ closest to 1), by assuming that the pores are then filled with liquid adsorbate (Details regarding calculation see Autosorb-1 Operating Manual Ver. 1.51 IV. Theory and Discussion, Quantachrome Instruments, Inc.). The average pore diameter (d) is calculated from the surface area (S) and the total pore volume ($V_{liq}$):

$$d = \frac{4Vliq}{S}$$

Average Grain Size

If desired, the average grain size can be determined with the Line Intercept Analysis.

FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Density

If desired, the density of the sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.). In this procedure the sample is first weighed in air (A), then immersed in water (B). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(A-B))\, \rho 0$, where $\rho 0$ is the density of water. The relative density can be calculated by reference to the theoretical density ($\rho t$) of the material, $\rho_{rel}=(\rho/\rho t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry cut saw. The diameter of the samples should be between 12 and 20 mm. Each wafer is centred on a support of three steel balls with a support diameter of 14 mm. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Method for Measuring Weight Percent Solids

The weight percent solids can be determined by drying a sample weighing 3-6 grams at 120° C. for 30 min. The percent solids can be calculated from the weight of the wet sample (i.e., weight before drying, $weight_{wet}$) and the weight of the dry sample (i.e., weight after drying, $weight_{dry}$) using the following equation: Wt-% solids=100 ($weight_{dry}$)/$weight_{wet}$.

Method for Measuring Oxide Content of a Solid

The oxide content of a sol sample can be determined by measuring the percent solids content as described in the "Method for Measuring Weight Percent Solids" then measuring the oxide content of those solids as described in this section.

The oxide content of a solid was measured via thermal gravimetric analysis (obtained under the trade designation "TGA Q500" from TA Instruments, New Castle, Del.). The solids (about 50 mg) were loaded into the TGA and the temperature was taken to 900° C. The oxide content of the solid is equal to the residual weight after heating to 900° C.

Volume Percent Metal Oxide

The volume percent of oxide present in an aerogel or a calcined metal oxide can be determined by back-calculation using shrinkage data and assuming that the final sintered body was a 1 cm cube, 100% dense. The total volume of the aerogel or calcined metal oxide is then $(Vt)=[1/(1-S)]^3$, where S is the fractional shrinkage from the aerogel or calcined state to the final sintered material. The volume of metal oxide is the volume of the sintered cube (V)=1. The percent metal oxide (Vol %)=$(1/V_t)100$.

Contrast Ratio Reflectance (CR-R)

CR-R value is the opacity using the contrast ratio method.

CR-R can be recorded using a Photospectrometer Color i7 (X-Rite Corp.) with an optical configuration of d/8° using pulsed xenon light source, D65 calibrated illumination, where a spectral range between 360 and 750 nm with 10 nm wavelength interval where recorded. For this measurement reflectance mode with 10 mm aperture is used. Color evaluation is configured with 10° observer, exclusion of specular and inclusion of UV irradiation.

To use the CR-R value, the calibration mode of the spectro has to include extended measurements for over light and over dark. Samples are analyzed using both a light backing and a dark backing. The calculation of CR-R is done automatically by the software, using a formula at the ratio of dark backing to light backing measurement.

CR-R is expressed as a percentage. The higher the level of CR-R, the more opaque the material and the lower the level of CR-R, the more translucent the material is.

Example 1

Sol Preparation
Materials Used

TABLE 1

| Material name or abbreviation | Description |
| --- | --- |
| Zirconium acetate | An aqueous solution of zirconium acetate containing nominally 16.3 wt.-% Zr obtained from Magnesium Elektron, Inc., Flemington, NJ. The aqueous solution was exposed to an ion exchange resin (obtained under the trade designation "AMBERLYTE IR 120" from Rohm and Haas Company, Philadelphia, PA) before use (oxide content 21.85 wt.-%). |
| DI water | De-ionized water |
| Yttrium acetate | Yttrium (III) acetate tetrahydrate obtained from AMR Technologies Inc., Toronto, Canada (oxide content 33.4 wt.-%) |
| 2-Hydroxyethyl methacrylate (HEMA) | An acrylate monomer obtained from Aldrich Chemical Company |
| Lanthanum Oxide | Lathanum (III) oxide obtained from Alfa Aesar, Ward Hill, MA (oxide content 99.45 wt.-%) |
| 2,2'-Azobis(2-methylbutyronitrile), ("VAZO 67") | 2,2'-Azobis(2-methylbutyronitrile), obtained from E. I. du Pont de Nemours and Company, Wilmington, DE under the trade designation "VAZO 67" |
| Acrylic Acid | Acrylic acid obtained from Alfa Aesar, Ward Hill, MA |
| Ethanol | Ethanol 200 proof obtained from Koptec, King of Prusia, PA |
| Erbium(III)acetate hydrate | Erbium-acetate-hydrate obtained from Treibacher Industrie Ag, Austria |
| Tri-ammonia-citrate | Tri-ammonia-citrate obtained from Fisher scientific GmbH, Germany |

Preparation of ZrO (88 mol-%)/$Y_2O_3$ (12 mol-% of Sol S-C)

Sol compositions are reported in mole percent inorganic oxide. Sol S-C was prepared as follows: (All other sols were prepared by similar methods in similar equipment.)

The hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2.000 grams) with DI water (2205.3 grams). Yttrium acetate (327.8 grams) was added while mixing until full dissolution. The solids content of the resulting solutions was measured gravimetrically (120° C./hr. forced air oven) to be 22.16 wt.-%. D.I. water (718 grams) was added to adjust the final concentration to 19 wt.-%. This procedure was repeated three times to give a total of about 15.115 grams of precursor material. The resulting solution was pumped at a rate of 11.48 ml/min. through the hydrothermal reactor. The temperature was 225° C. and the average residence time was 42 min. A clear and stable zirconia sol was obtained.

Table 2 is a summary of the compositions prepared and the process conditions used for other sols produced in a similar manner as Sol S-C.

TABLE 2

| Sol | $ZrO_2$ [mol %] | $Y_2O_3$ [mol %] | $La_2O_3$ [mol %] | Residence time [min] | Temperature, [° C.] |
| --- | --- | --- | --- | --- | --- |
| S-T | 95.7 | 2.3 | 2.0 | 42 | 225 |
| S-C | 88 | 12 | 0 | 42 | 225 |

Sol Concentration and Diafiltration

The resulting sols were concentrated first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

The content of cubic zirconia crystallites (100 wt.-% cubic phase) found in Sol S-C was 33 wt.-%. The content of tetragonal zirconia crystallites (100 wt.-% tetragonal phase) found in Sol S-T was 35 wt.-%.

Part A:

22.60 g of a sol containing cubic zirconia crystallites (S-C; 33 wt.-% solids) and 64.20 g of a sol containing tetragonal zirconia crystallites (S-T; 35 wt.-% solids) were mixed and stripped of excess water with a rotovap until a mass of 49 to 50 g was reached. 15.15 g ethanol, 2.88 g acrylic acid and 1.47 g hydroxyethylmethacrylate were added to the solution and mixed by stirring for 2 h. 0.10 g of initiator (AIBN) were added and mixed by stirring for another 45 min.

The mixture was then divided into 6 syringes of 20 mm diameter, which had 2 pistons, one from each side. The mixtures were cured in a drying oven (Memmert) at 50° C. for 4 h.

Part B:

67.80 g of a sol containing cubic zirconia crystallites (S-C; 33 wt.-% solids) and 21.40 g of a sol containing tetragonal zirconia crystallites (S-T; 35 wt.-% solids) were mixed and stripped of excess water with a rotovap until a mass of 49 to 50 g was reached. 15.15 g ethanol, 2.88 g acrylic acid and 1.47 g hydroxyethylmethacrylate were added to the solution and mixed by stirring for 2 hours. 0.10 g of initiator (AIBN) were added and mixed by stirring for another 45 minutes.

The mixture was divided into 6 double-piston syringes of 28 mm diameter and the 6 pieces of cured mixture from Part A were also put into the syringes, so that they would be surrounded by the liquid mixture from Part B. The syringes were put into a drying oven (Memmert) at 50° C. for 4 hours.

The cured mixtures were taken from the syringes and put into pure ethanol. The ethanol was replaced with fresh ethanol 3 times every 24 h to exchange residual water with ethanol. The solvent exchanged mixtures were immersed into liquid carbon dioxide and supercritically extracted.

The extracted mixtures were calcined at 900° C. (Nabertherm oven) to remove all organics. The blocks were cut into discs of about 1 mm thickness and sintered to final density at 1250° C. (Nabertherm oven). The surfaces were polished to reveal the translucency of the material.

The amounts of tetragonal and cubic sol were selected to achieve a tetragonal/cubic ratio by weight of 75/25 for Section A (inner section) and 25/75 for Section B (outer section).

The obtained disc is shown in FIG. 1. The disc has two sections, Section A and Section B. Section A is less transparent than Section B.

Comparison Example

For comparison a disc of conventional 3Y-TZP zirconia was prepared by
first compacting 3Y-TZP zirconia powder (Tosoh company),
sintering the compacted zirconia powder to full density (1500° C.; 2 hrs),
cutting the obtained sintered sample into discs having a thickness of about 1 mm and
polishing the surfaces of the disc.

Figure 2:
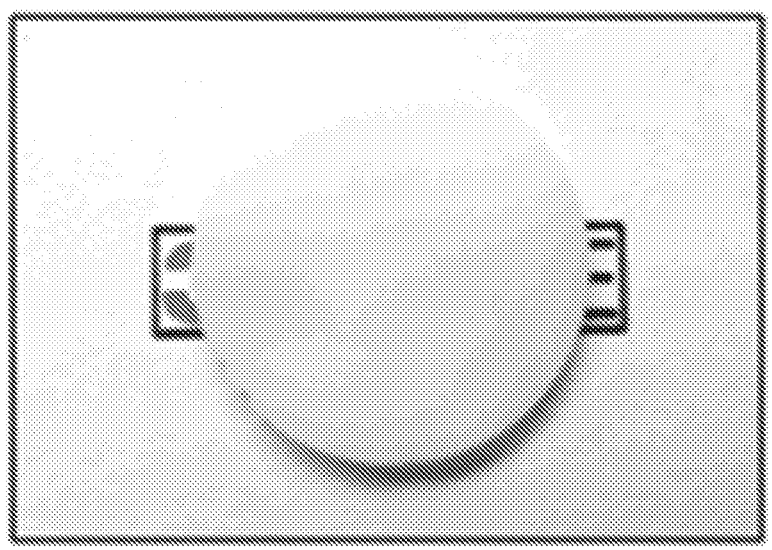
FIG. 2 shows a sintered zirconia disc obtained when sintering a commercially available zirconia material.

The obtained disc is shown in FIG. 2.

Compared to both section of the disc shown in FIG. 1, the sample shown in FIG. 2 is more opaque.

The crystalline phase content for this sample was determined to about 20 wt.-% cubic and about 80 wt.-% tetragonal phase.

The invention claimed is:

1. A porous dental milling block comprising at least two geometrically defined Material Sections A and B,
Material Section A comprising a tetragonal zirconia crystal phase in an amount A-T in wt.-% and a cubic zirconia crystal phase in an amount A-C in wt.-%,
Material Section B comprising a tetragonal zirconia crystal phase in an amount B-T in wt.-% and a cubic zirconia crystal phase in an amount B-C in wt.-%,
wherein (amount of tetragonal phase $A$-$T$ in wt.-%)/(amount of cubic phase content $A$-$C$ in wt.-%)>1 and (amount of tetragonal phase content $B$-$T$ in wt.-%)/(amount of cubic phase content $B$-$C$ in wt.-%) <1, the material of Material Sections A and B showing a $N_2$ adsorption and/or desorption behaviour of isotherm IV according to IUPAC classification.

2. The porous dental milling block of claim 1, the material of Material Sections A and B having the following property:
the sintering temperature being in a range of 1200 to 1400° C.

3. The porous dental milling block of claim 1 having at least one of the following features:
the ratio of the tetragonal phase content A-T in % to the cubic phase content A-C in % in Section A being in a range from about 1.2 to about 50,
the ratio of the tetragonal phase content B-T in % to the cubic phase content B-C in % in Section B being in a range from about 0.02 to about 0.8.

4. The porous dental milling block of claim 1 having at least one of the following features with respect to Material Section A before sintering to final density:
showing a $N_2$ adsorption and desorption behaviour with a hysteresis loop of type H1 according to IUPAC classification;
showing a $N_2$ adsorption and desorption behaviour with a hysteresis loop in a p/p0 range of 0.70 to 0.95;
average connected pore diameter: from about 10 to about 100 nm;
average grain size of crystalline zirconia: less than about 100 nm;
BET surface: from about 10 to about 200 $m^2/g$;
Biaxial flexural strength: from about 10 to about 40 MPa;
x, y, z dimension: at least about 5 mm;
Vickers hardness: from about 25 (HV 0.5) to about 150 (HV 1);
having an isotropic sintering behaviour;
density: 2.2 to 3.3 $g/cm^3$;
sintering temperature: from about 1200 to about 1400° C.;
having an $ZrO_2$ content: from about 85 to about 98 mol %;
having a $HfO_2$ content: from about 0 to about 3 mol %;
having an $Y_2O_3$ content: from about 1 to about 15 mol %;
having an $Al_2O_3$ content: from about 0 to about 1 mol %.

5. The porous dental milling block of claim 4 further having at least one of the following features with respect to Material Section A before sintering to final density:
average connected pore diameter: from about 10 to about 80 nm;
Biaxial flexural strength: from about 15 to about 30 MPa;
x, y, z dimension: at least about 10 mm.

6. The porous dental milling block of claim 5 further having at least one of the following features with respect to Material Section A before sintering to final density:
average connected pore diameter: from about 10 to about 50 nm;
x, y, z dimension: at least about 20 mm.

7. The porous dental milling block of claim 1 having at least one of the following features with respect to Material Section B before sintering to final density:
showing a hysteresis loop when analyzed with regard to its adsorption and desorption behaviour to nitrogen;

showing a $N_2$ adsorption and desorption behaviour with a hysteresis loop of type H1 according to IUPAC classification;
showing a $N_2$ adsorption and desorption behaviour with a hysteresis loop in a p/p0 range of 0.70 to 0.95;
average connected pore diameter: from about 10 to about 100 nm;
average grain size of crystalline zirconia: less than about 100 nm;
BET surface: from about 10 to about 200 $m^2/g$;
Biaxial flexural strength: from about 10 to about 40 MPa;
x, y, z dimension: at least about 5 mm;
Vickers hardness: from about 25 (HV 0.5) to about 150 (HV 1);
having an isotropic sintering behaviour;
density: 2.2 to 3.3 $g/cm^3$;
sintering temperature: from about 1200 to about 1400° C.;
having an $ZrO_2$ content: from about 85 to about 98 mol %;
having a $HfO_2$ content: from about 0 to about 3 mol %;
having an $Y_2O_3$ content: from about 1 to about 15 mol %;
having an $Al_2O_3$ content: from about 0 to about 1 mol %.

8. The porous dental milling block of claim 7 further having at least one of the following features with respect to Material Section B before sintering to final density:
average connected pore diameter: from about 10 to about 80 nm;
Biaxial flexural strength: from about 15 to about 30 MPa;
x, y, z dimension: at least about 10 mm.

9. The porous dental milling block of claim 8 further having at least one of the following features with respect to Material Section B before sintering to final density:
average connected pore diameter: from about 10 to about 50 nm;
x, y, z dimension: at least about 20 mm.

10. The porous dental milling block of claim 1, Material Section A and Material Section B having the shape of layers or blocks; being arranged in a core-shell structure; having tooth-like shapes; or a combination thereof.

11. The porous dental milling block of claim 1 not comprising oxides selected from $TiO_2$, $SiO_2$ or mixtures thereof in an amount above 2 mol % with respect to the weight of the porous dental milling block.

12. The porous dental milling block of claim 1 comprising means for attaching it to a machining device, the means for attaching being selected from grooves, notches, recesses, stamps and holding devices, stumps and combinations thereof.

* * * * *

UNITED STATES PATENT AND TRADEMARK OFFICE
CERTIFICATE OF CORRECTION

PATENT NO. : 10,028,809 B2
APPLICATION NO. : 14/436109
DATED : July 24, 2018
INVENTOR(S) : Michael Jahns Page 1 of 2

It is certified that error appears in the above-identified patent and that said Letters Patent is hereby corrected as shown below:

In the Specification

Column 2
Line 67, Delete "%)<1," and insert -- %)<1. --, therefor.

Column 19
Line 3, After "density" insert -- ; --.

Column 19
Line 28, Delete "ketons." and insert -- ketones. --, therefor.

Column 20
Line 29, Delete "triethylentetramine," and insert -- triethylenetetramine, --, therefor.

Column 20
Lines 30-31, Delete "phthalocyanin," and insert -- phthalocyanine, --, therefor.

Column 20
Line 31, Delete "propylendiamine," and insert -- propylenediamine, --, therefor.

Column 20
Line 37, Delete "ethylendiamin" and insert -- ethylenediamine --, therefor.

Column 21
Line 14, After "5" insert -- . --.

Column 21
Line 45, Delete "hydrochinone," and insert -- hydroquinone, --, therefor.

Signed and Sealed this
Twenty-third Day of April, 2019

Andrei Iancu
*Director of the United States Patent and Trademark Office*

CERTIFICATE OF CORRECTION (continued)
U.S. Pat. No. 10,028,809 B2

Column 24
Line 40, Delete "defraction" and insert -- diffraction --, therefor.

Column 27
Line 18, Delete ""AMBERLYTE" and insert -- AMBERLITE --, therefor.

Column 27
Line 26, Delete "Lathanum" and insert -- Lanthanum --, therefor.

Column 27
Line 32, Delete "Prusia" and insert -- Prussia --, therefor.

Column 27
Line 39, Delete "ZrO" and insert -- $ZrO_2$ --, therefor.

Column 27
Lines 39-40, Delete "mol-% of Sol S-C)" and insert -- mol-%) Sol (Sol S-C) --, therefor.

Column 28
Line 40, Delete "$Y_20_3$" and insert -- $Y_2O_3$ --, therefor.

Column 28
Line 66, Delete "(AlBN)" and insert -- (AIBN) --, therefor.